United States Patent [19]

Burckhardt

[11] Patent Number: 5,501,963

[45] Date of Patent: Mar. 26, 1996

[54] AMPLIFICATION AND DETECTION OF NUCLEIC ACIDS IN BLOOD SAMPLES

[75] Inventor: Jean Burckhardt, Magden, Switzerland

[73] Assignee: Hoffmann-La Roche Inc., Nutley, N.J.

[21] Appl. No.: 118,534

[22] Filed: Sep. 8, 1993

[30] Foreign Application Priority Data

Sep. 11, 1992 [CH] Switzerland ............................ 2875/92

[51] Int. Cl.$^6$ ............................. C12P 19/34; C12Q 1/00; C12Q 1/48; C12Q 1/68

[52] U.S. Cl. ................... 435/91.2; 435/4; 435/5; 435/6; 435/91.1; 435/267; 435/269; 435/270; 536/23.1; 536/24.33

[58] Field of Search ................ 435/91.2, 5, 270, 435/267, 269, 91.1, 6, 4; 536/23.1, 24.33; 935/77, 78

[56] References Cited

U.S. PATENT DOCUMENTS

| | | | |
|---|---|---|---|
| 5,035,996 | 7/1991 | Hartley | 435/6 |
| 5,284,940 | 2/1994 | Lin et al. | 536/25.4 |

FOREIGN PATENT DOCUMENTS

| | | |
|---|---|---|
| 0401037 | 12/1990 | European Pat. Off. . |
| 0415755 | 3/1991 | European Pat. Off. . |
| 9006373 | 6/1990 | WIPO . |

OTHER PUBLICATIONS

Mercier, et al., Nuc. Acids Res., 18:5908, "Direct PCR from whole blood, without DNA extraction" (1990).
Panaccio and Lew, Nuc. Acids Res., 19:1151 (1991) "PCR based diagnosis in the presence of 8% (v/v) blood".
McCusker, et al., Nuc. Acids Res., 20:6747 (1992) "Improved Method for direct PCR amplification from whole blood".
Ravaggi, et al., PCR Method and Applications, 1:291–292 (1992) "Direct PCR Amplification of HCV RNA from Human Serum".
Panaccio, et al., BioTechniques, 14:238–243 (1993) "FoLT PCR: A Simple PCR Protocol for Amplifying DNA Directly from Whole Blood".
Cimino et al. Nucl. Acids Res. 19(1):99 (1990).
Izraeli et al. Nucl. Acids Res. 19(21) (1991).

*Primary Examiner*—W. Gary Jones
*Assistant Examiner*—Paul B. Tran
*Attorney, Agent, or Firm*—George M. Gould; William H. Epstein; Raina Semionow

[57] ABSTRACT

This invention relates to a process for the amplification of nucleic acids in the form of DNA or RNA from blood samples by means of an enzymatic amplification method, characterized in that no preparation of the blood sample otherwise necessary to prepurify the nucleic acid to be amplified is performed and the proportion of the sample in the reaction mixture for the amplification process is greater than 5 volume % if a specific amount of salt is present in the reaction mixture. Depending on the proportion of blood sample and its salt contribution of monovalent and/or bivalent ions, the salt concentration in the reaction mixture in which the amplification is performed is, where applicable, adapted to the enzyme requirements by the use of an appropriately concentrated salt solution.

16 Claims, No Drawings

AMPLIFICATION AND DETECTION OF NUCLEIC ACIDS IN BLOOD SAMPLES

This invention relates to the amplification and detection of nucleic acids and blood samples.

The subject of this invention is a process for the amplification of nucleic acid sequences, DNA or RNA, from blood samples by means of an enzymatic amplification method having a salt concentration. The process is characterized in that no preparation of the blood sample otherwise necessary to prepurify the nucleic acid sequences to be amplified is performed and the proportion of the sample in the reaction mixture for the amplification process is greater than 5 volume %, preferably greater than 10 volume %.

BACKGROUND OF THE INVENTION

There is an increasing need in biological research, and more particularly diagnostic medicine, for identifications and characterizations of nucleic acids. By "nucleic acids" there are to be understood in the present case the deoxyribose nucleic acids (DNA) and the ribose nucleic acids (RNA) in either naturally occurring form or as they can be produced by modern methods of chemical and biological synthesis of substantially any sequence and length.

Conventional methods used in molecular biology to prepare nucleic acids from blood are complex and include steps such as centrifuging, phenol/chloroform extraction of the samples or precipitations of the nucleic acids with organic solvents, which are useless for rapid and possibly automatable enzymatic amplification of nucleic acids without substantial preparation. A recent compilation of such methods is found in "An efficient and simple method of DNA extraction from whole blood and cell-lines to identify infectious agents" by V. N. Loparev et al., J. Vir. Methods 34:105–112 (1991) and in "Chelex 100 as a medium for simple extraction of DNA for PCR-based typing from forensic material" by P. S. Walsh et al., BioTechniques 10(4):506–513 (1991).

It has been reported in the literature that whole blood inhibits the polymerase chain reaction (PCR) when present even in very small quantities — i.e., 1 volume % in the reaction mixture. The reason for this inhibition is believed to be due to heme derivatives consisting of porphyrin rings that are present in blood (R. Higuchi, *PCR Technology*, Chapter "Simple and rapid preparation of samples for PCR", pages 31–38, H. Ehrlich Ed., Stockton Press, 1989).

According to Higuchi, supra, a method of preparing target DNA molecules in blood samples for PCR is to isolate the mononuclear blood cells (MC) by way of ficoll gradients or to isolate the leucocytes by centrifuging after lysis of the erythrocytes and to incubate the MCs with proteinase K. After digestion, the proteinase K is inactivated at 95° C. and an aliquot of the sample is used in the PCR process.

Mercier et al. describe PCR amplification of various fragments of chromosomal DNA from fresh blood or frozen blood in a concentration of 1 to 2 volume % in a PCR reaction mixture (Nucleic Acids Research 18:5908 (1990)) in which the amplification solution containing the blood sample (without Taq polymerase) was repeatedly brought for 3 minutes at a time to temperatures of 95° C. and 55° C., a step which facilitated subsequent amplification by PCR.

Panaccio et al. (Nucleic Acids Research 19:1151 (1991)) describe the amplification of DNA from whole blood using thermostable DNA polymerase from *Thermus thermophilus*. They show that DNA from 4 µl of blood in 100 µl of reaction mixture (4 volume %) is amplifiable using *Thermus thermophilus* DNA polymerase. On the other hand, as little as 1 volume % of blood completely inhibits amplification by means of the DNA polymerase from *Thermus aquaticus* (Taq).

Beutler et al. (BioTechniques 9:166 (1990)) describe in detail the effect of anticoagulants on the amplification by PCR of DNA targets from blood samples. It was impossible to amplify these targets even when the DNA was concentrated from heparinized blood by means of a nucleic acid extract. Further processes for purifying DNA that facilitate use of PCR with the DNA thus isolated are also described, including the treatment of DNA with heparinase II. There were no problems with amplifying DNA isolated from EDTA-treated blood.

Israeli et al. (Nucleic Acids Research 19:6051 (1991)) describe the amplification by PCR of RNA which was isolated from frozen heparin-treated whole blood by extraction after conversion of the RNA into eDNA. Israeli demonstrate that the difficulties in conducting PCR were due to the heparin. Only when the isolated RNA was treated with heparinase before transcribing into eDNA, was the PCR successful.

Franchis et al. (Nucleic Acids Research 16:10355 (1988)) also describe the inhibition of the PCR process using Taq polymerase when amplifying samples of genomic DNA isolated from human blood. The inhibitor, which was not specifically identified in the article, could be removed by boiling and filtering the DNA.

Ravaggi et al. (PCR Methods and Applications 4:291–292 (1992)) describe the amplification of HCV RNA from human serum by means of PCR. The RNA was transcribed directly from the serum into eDNA with reverse transcriptase without previous purification. An aliquot containing approximately 3 volume % of DNA then was introduced into a PCR mix.

One of the goals of this invention is to overcome the difficulties noted in the prior art described above in order to use increased quantities of blood directly in an enzymatic amplification process for nucleic acids, such as, for example, PCR, and more particularly, when the blood is treated with anticoagulants.

SUMMARY OF THE INVENTION

The subject of this invention is a process for the amplification of target nucleic acid sequences, RNA or DNA, present in blood by means of an enzymatic amplification method, said amplification method using at least one salt. This process is advantageous in that the blood sample need not be treated prior to amplification to isolate or purify the target nucleic acid sequences. The amount of sample in the amplification reaction mixtures is greater than or equal 5 volume %, preferably greater than or equal to 10 volume %.

This invention may also be used to determine genetic sequences, for example, of humans, from blood and to identify foreign nucleic acids of microorganisms in the blood, including nucleic acids from bacteria, DNA or RNA viruses or eucaryotic nucleic acids. The claimed process is particularly useful in the detection of small quantities of an infectious microorganism in a blood sample.

DETAILED DESCRIPTION OF THE INVENTION

The term "blood sample" is used herein to denote any kind of sample whose origin can be derived from blood. It can be, for example, liquid blood, such as fresh whole blood with all its constituents, or plasma. It also includes dried blood such as is present, for example, in blood stains, to coagulated blood or the serum obtained therefrom, and to blood stabilized by vitrification as is described by R. Ramanujan et al. (Clin. Chem. 39:737 (1993)).

Blood in its natural form consists of a liquid component, the plasma, and a corpuscular component, the blood cells (erythrocytes, leucocytes, thrombocytes etc.). The "plasma" is that portion of the anticoagulated blood which remains after centrifuging. It is a clear light yellow liquid which contains in addition to albumins, coagulants and plasma proteins, sugar, minerals and other products of metabolism. The "serum" is the liquid part of the blood which is obtained by centrifuging after coagulation and lacks the coagulant factors such as fibrinogen.

The whole blood of adults excluding leucocytes, consists of 55% plasma with 141.7 to 148.8 mM sodium and potassium and 45% erythrocytes with 90.4 to 106 mM sodium and potassium. The average value of sodium and potassium is of about 124 mM (Documenta Geigy 1973, pages 560–564).

The term "monovalent ions" used herein denotes only ions that are present in blood having a single positive charge — i.e., mainly Na+ and K+. The chloride content is disregarded. Correspondingly, the term "bivalent ions" denotes ions carrying two positive charges — i.e., mainly $Mg_2+$ and $Ca_2+$.

Fresh blood is typically treated with anticoagulants to prevent premature coagulation. The best known anticoagulants are heparin, the salts of citronic acid (citrates), and the salts of ethylenediamine-tetraacetic acid (the salt hereafter abbreviated EDTA).

According to the information provided by some manufacturers of containers for blood sample collection, for example, Sherwood Medical, EDTA, citrate and heparin are typically added to blood samples as follows:

EDTA is added to blood as a tripotassium salt (0.1 ml of a 15% solution per 10 ml of blood). This results in an additional concentration of approximately 10 mM of added potassium of the blood sample.

Citrate is added to the blood as a trisodium salt (normally 0.5 ml of a 3.8% solution to 4.5 ml of blood). This results in the addition of approximately 36 mM of sodium to the blood sample.

Heparin is added as lithium salt in a final concentration of 14.3 USP units per ml of blood. This corresponds to approximately 0.1 mg of hepaxin per ml of blood or 5–15 µM of salt.

Based on the foregoing, typical blood sample preparations have approximately the following final concentrations of monovalent ions: (a) EDTA treated blood: 135 mM; (b) citrate treated blood: 160 mM; and (c) heparin treated blood: 124 mM. Further particulars on recommended salts and their concentration as anticoagulants are given in "N.S. Evacuated Tubes for Blood Sample Collection", Third Edition (1991), Vol. 11 (No. 9):6 (NCCLS Document A1–A3).

The final concentration of monovalent ions in the reaction mixture (mainly potassium and sodium) for amplification of the target nucleic acids depends upon the buffer, the volume of the sample and the kind of anticoagulant in the whole blood. Note that inasmuch as the concentration of anticoagulants may vary with different makers, in the following description of the concentration of monovalent ions, only the amounts of salts from the blood alone (approximately 124 mM) and the added amounts from the addition of solutions having defined salt concentrations, will be considered. The monovalent ion concentration due to the anticoagulants will be disregarded. In the case of heparin, this value is insignificant in any event.

The target nucleic acids to be amplified by the processes of the present invention can be present in the blood cells (e.g. genomic DNA, mRNA), in plasma, and in serum.

In plasma or serum, the nucleic acids can be the cell's own DNA or RNA which are liberated by cell lysis, or they can be foreign nucleic acids that are introduced by bacteria or viruses. Some RNA viruses do not transcribe DNA. In these cases, the first amplification can take place after transcription of the RNA into DNA. Further amplification cycles can be performed on the DNA stage alone or by way of new RNA intermediate stages, as will be described by way of example hereinafter.

As previously stated, identifying particular nucleic acids from blood samples containing a mixture of other nucleic acids is presently difficult. Even when an amplification process that can act specifically in the presence of very large quantities of different sequences is used, certain target nucleic acids, for example, those of a non-repetitive gene, must be concentrated before amplification is carried out. For purposes of diagnosis, the amplification process must selectively amplify only the desired nucleic acid sequence, for example, a 100 Bp long DNA fragment which occurs in every human cell only once in a total of 31 million other sequences of the same magnitude (the human genome consists of $3.1 \times 10^9$ base pairs or $3.4 \times 10^{-12}$ g of DNA). Presently, in order to use the polymerase chain reaction (PCR), the best known enzymatic amplification process, it is necessary to perform a relatively elaborate process to prepare the samples prior to amplification. The aim of these additional steps, which normally have to be used, is to remove or neutralize suspected amplification inhibitors in the blood by prepurification of the nucleic acids, and thus facilitate unimpeded amplification of the nucleic acid sequences of interest. Sample preparation procedures for the target nucleic acids to be amplified differ according to whether the sample is from cells, plasma/serum, or from whole blood.

Before this invention, PCR amplification typically was inhibited by excessive salt concentrations in samples having a large blood component. Calculations show that blood with an average natural concentration of monovalent ions of approximately 124 mM will have an adverse affect on amplification carried out using Taq polymerase. Having regard to conventional PCR buffers, for example, the 10 X buffer, which is designed to give a final concentration in the prepared reaction mixture of 50 mM K+, the concentration of monovalent ions (K+, Na+) in the reaction mixture having a 10 volume % blood content totals approximately 63 mM, and approximately 113 mM when the blood content is 50 volume %. As was previously stated, these values do not include the salt contribution of any anticoagulant used in the sample.

On the other hand, the DNA polymerase of *Thermus aquaticus* (Taq polymerase), which is the polymerase most used in PCR, has optimum synthesis around approximately 50 mM KCl (PRC Technology 1989; Chapter 2: Taq DNA Polymerase, by D. H. Gelfand). This is why normal PCR buffers have the KCl concentration mentioned in the reference. No activity for Taq polymerase can be detected in conventional sequencing reactions at more than 75 mM KCl, or in 10-minute incorporation assays at more than 200 mM KCl.

We have surprisingly found that if overall salt concentration is controlled — i.e., adjusted in the reaction mixture — nucleic acids can be amplified directly from untreated blood samples. An increase of initial nucleic acids is obviously available in higher volume samples, for example, ≧10 volume %, of a blood sample in the PCR reaction mixture. Knowing the salt concentration of a blood sample, that is of monovalent and bivalent ions contributed by the blood to the reaction mixture in which the amplification is performed, the overall salt concentration in the reaction mixture can be maintained in a predetermined range and adapted to the requirements of the enzyme to be used by the utilization, inter alia, of an appropriately concentrated salt solution. By way of example, the salts of the elements of the first and second groups of the periodic table can be used for this purpose, with Na+, K+ and Mg2+ being preferred.

Depending upon the amount of blood sample in the overall reaction mix, the salt concentration in the reaction mix can readily be controlled by an appropriately concentrated or dilute salt solution. This means that if there is a high blood proportion in the reaction mixture, no further monovalent salts are added — i.e., if the blood proportion is high enough the buffer capacity and the salt content of monovalent or bivalent ions of the sample may in some circumstances be sufficient to facilitate a specific amplification — i.e., it is unnecessary to use a further salt solution.

The salt solution can contain, in addition to salts, buffers and other components necessary and/or advantageous for the particular amplification process. These components can be, for example, Tricine (N-(Tris(hydroxymethyl)-methyl-glycin), Tris (Tris-(hydroxymethyl)-aminomethane-hydrochloride), ionic or non-ionic detergents, such as, for example, Triton X-100 (alkylphenylpolyethyleneglycol) or Tween (polyoxyethylenesorbitol monolaureate), and salts of other elements such as, for example, salts of Mn or Co and so on, as are important for the activity of the particular enzymes used in the particular amplification.

This invention is applicable to any enzymatically based amplification process. A number of enzymatic amplification processes are described in the literature. One process such process, the ligase chain reaction (LCR), as described, inter alia, in EP-A 320 308 or EP-A 336 731. Further explanations and applications of this method have been described by Wu and Wallace, Genomics 4:560–569 (1989).

Other enzymatic amplification processes are TAS and 3SR. These are described in EP-A 310 229 and EP-A 373 960, respectively. Other descriptions can be found in Guatelli et al., Proc. Natl. Acad. Sci. US 87: 1874–1878 (1990) and Kwok et al., Proc. Natl. Acad. Sci. USA 86:1173–1177 (1989), respectively. In these processes, a number of enzymes are used either simultaneously or consecutively in the amplification process, for example, a DNA polymerase and an RNA polymerase and other enzymes are used.

Another amplification process is based on the use of the replicase of the RNA bacteriophage Qβ. The operation of this process has been described e.g. in EP-A 361 983 or in Lizardi et al., TIBTECH 9, 53–58 (1991).

Another enzymatic amplification process, and that which is preferred in the application of the present invention, is the polymerase chain reaction (PCR), which is one of the processes described in U.S. Pat. Nos. 4,683,195 and 4,683,201. In a preferred embodiment, the nucleic acids are amplified by means of a thermostable polymerase. Useful polymerases from various thermostable bacteria include *Thermus aquaticus* (U.S. Pat. Nos. 4,889,818 and 5,079, 352), *Thermus thermophilus* (WO/9108950), *Pyrococcus furiosus* (WO 92/9688) and *Thermococcus litoralis* (EP-A 455 430). These enzymes are useful in either their purified natural or recombinant form and are commercially available. Polymerases which can be isolated from the genus Thermus are preferred. The thermostable DNA polymerase from *Thermus aquaticus* ("Taq") is particularly preferred in the present invention.

The PCR process can be used to amplify and detect RNA based nucleic acid targets by first transcribing the RNA into DNA. Such a process is described, for example, in WO 91/09944. The so-called reverse transcriptases can, for example, also be used as enzymes in this case. The reverse transcriptase activity of a DNA polymerase such as the Taq polymerase, can also be used for this purpose. The corresponding presence of other bivalent ions (in this case e.g. of Mn2+) should, where applicable, be ensured to make full use of this activity.

The practice of the process according to the present invention when carried out with PCR or TAS, is used with varying temperatures and is conveniently performed in an automated system in which the temperature for denaturing, the hybridization of the primers and the polymerization reaction can be accurately controlled. An appropriate device for this purpose is described in U.S. Pat. No. 5,038,852. Apparatuses of this kind are also commercially available.

The oligonucleotides for carrying out the enzymatic amplification of the nucleic acids and the subsequent detection thereof can be prepared by known methods, for example, by solid phase synthesis (Oligonucleotide Synthesis: A practical Approach, IRL Press, Oxford, UK, Ed. M. J. Gasit (1984)). Many such oligonucleotides are also commercially available.

All the enzymatic amplification processes hereinbefore mentioned use specific salt concentrations and/or buffers for optimum matching to the requirements of the particular enzyme used. In each of the various amplification processes, the DNA or RNA sought to be amplified is often isolated from other components in the sample by a pre-purification step or is at least highly concentrated. The enzymatic buffer does not then need to be adapted to any of additives that are introduced by the sample. However, if such pre-purification is performed, then correspondingly elaborate preparation steps are also necessary, inter alia. because of the risk of contamination of the sample.

For purposes of describing how the invention operates, it is herein demonstrated in conjunction with PCR to amplify target nucleic acids in blood samples.

A special feature of this invention is in amplification of nucleic acids from heparinized blood. It is presently known that PCR amplification of nucleic acids in blood samples is inhibited when the samples are previously treated with heparin as an anticoagulant. This fact is consistent with earlier findings in enzymology wherein heparin was used as a specific inhibitor of DNA-binding proteins because the latter have a greater affinity for heparin than for their substrate, the nucleic acids (T. A. Bickle et al., Nucleic Acid Res. 4:2561, 1977; J. Leis et al., Methods in Enzymology XXIX:153, 1974). Such prior findings would be expected to instill in a skilled artisan the prejudice that amplification of DNA from heparin-treated blood samples by means of PCR in the reaction mixture is impossible. However, we found, unexpectedly, that the amplification of DNA is possible in reactions with high (e.g. ≧10 volume %) to very high blood content (e.g. ≧50 volume %). This is possible even with the use of conventional PCR buffers — that is, no special adaptation of the KCl concentration in the conventional PCR buffer (approximately 50 mM of KCl) to the salt concentration introduced by the sample components is needed (see, e.g., Example 2). Another alternative is to neutralize the added amount of the salt with buffers when the salt content of the sample is very high. The salt concentration of monovalent ions in the reaction mixture is approximately 10–160 mM. Preferably, the monovalent ion concentration is approximately 10–90 mM.

Another special feature of this invention is the amplification of nucleic acids from EDTA treated blood. In this kind of blood, no specific DNA amplification can be performed with elevated amounts of blood sample (upwards from about 30 volume %) when the conventional concentration of 50 mM of KCl in the PCR buffer is used. This corresponds to a maximum salt concentration of monovalent ions of approximately 135 mM (see Table 1, Example 1 and Table 2, Example 2, respectively).

The effect of the salt on the PCR enzyme is also noted even when DNA is used as substrate which has been purified in order to prevent the influence of blood compounds. Specific amplification of desired target is possible only above 10 mM of KCl in the reaction mixture (Example 1, Table 1). Correspondingly, no addition of KCl to the reaction mixture is necessary, for example, upwards from 20 volume % of EDTA-treated blood component because the sample itself is providing approximately 25 mM of monovalent ions (Table 1). Consequently, for the amplification of DNA or RNA from EDTA-treated blood, the salt concentration of monovalent ions in the reaction mixture should be between 10 and 135 mM, preferably between 30 and 80 mM.

Yet another object of this invention is the amplification of nucleic acids from citrated blood. When blood treated with citrate as an anticoagulant is used as sample material for enzymatic amplification, different results are obtained depending on the sample concentrations. If, for example, the conventional buffer containing 50 mm of KCl is used in the PCR, amplification is possible with a sample concentration of up to approximately 20 volume % in the reaction mixture. However, a higher KCl concentration is usually advisable in the case of optimized magnesium concentrations and can be supplied, for example, by way of the PCR buffer. For example, an additional KCl concentration of 100–150 mM in the reaction mixture is suitable for amplifying blood samples having concentrations equal to and greater than 50 volume % (Example 2). This also corresponds approximately to a concentration equal to or higher than 70 mM of monovalent ions in the sample. A salt concentration of monovalent ions in the reaction mixture of between 30 and 200 mM is therefore suggested for enzymatic amplification. Preferably, a salt concentration of monovalent ions from about 60 to about 150 mM is used.

Also, it is found with citrated blood that it may, in some circumstances, be advantageous to adapt the concentration of bivalent ions. For efficient PCR, for example, the amount of Mg2+ should be raised above the otherwise normal figure of 1.5–2 mM in the reaction mixture, especially when very high blood concentrations (e.g. ≧20 volume %) are present in the reaction mixture. A concentration of more than 3 mM of Mg2+ is typically necessary and can go as high as 40 mM without damage. There is therefore considerable freedom in the choice of the Mg2+ concentration provided it is above a critical minimum.

Disregarding the Mg$^2$+ concentrations in blood the Mg2+ concentration in the reaction mixture is very important when EDTA is present in the blood sample as an anticoagulant. Approximately 0.35– 0.4 mM of Mg2+ is bound by 10 volume % of EDTA-treated blood, approximately 1.75–2.0 mM of Mg2+ is bound by 50 volume % of EDTA-treated blood, and approximately 3.5–4.0 mM of Mg2+ is bound by 80 volume % of EDTA-treated blood. The quantities of Mg2+ bound to EDTA are therefore always equimolar. However, since a free Mg2+ concentration is necessary for successful amplification, the bound Mg2+ in the reaction mix must be taken into consideration. For an optimum PCR, more than 1 mM of free Mg2+ should be present. If the free Mg2+ concentration is 1 mM or less, at most only 50% of the maximum possible amplification yield is obtained. The top limit is approximately 20 mM of free Mg2+. Higher values produce suboptimal amplification yields. For an optimum PCR, an Mg2+ concentration of 1.4 mM has been found to be the necessary minimum concentration in the presence of 10 volume % of EDTA-treated blood. 3.0 mM of Mg2+ was found to be the necessary minimum concentration in the presence of 50 volume % of EDTA-treated blood and 5.0 mM of Mg2+ was found to be the necessary minimum concentration at 80 volume % of EDTA-treated blood. What is particularly surprising about these figures is that the free Mg2+ concentration of EDTA-treated blood quantity of concentrations as high as 80 volume % can be used as a reaction mix for amplification without any pretreatment.

Additional KCl concentrations (in mM) supplied by the PCR buffer to the reaction mixture in the case of optimized MgCl$_2$ concentrations for the amplification of DNA in reactions having a concentration of 10 to 50 volume % of unpurified blood samples treated with various anticoagulants led to the results given in the following Table. The Table below gives an overview of how, for example, with increasing sample concentration in the reaction mixture, the optimum concentration of monovalent ions (here, for example, by means of KCl) of the added PCR buffer varies in the manner as discussed above.

| Sample concentration (volume %) in the reaction solution | 10% | 20% | 30% | 40% | 50% |
| --- | --- | --- | --- | --- | --- |
| EDTA blood | 50 | 25 | 0 | 0 | 0 |
| Heparin blood | 70 | 50 | 10 | 0 | 0 |
| Citrated blood | 100 | 100 | 80 | 50 | 50 |

As an additional step to ensure efficient amplification, the blood sample can be frozen before use if this has not already been done by virtue of the nature of sample storage. Another possible way of enhancing amplification is first to denature the sample alone or the prepared reaction mixture in a thermocycler a few times by heating and cooling. About 5–20 such cycles with heating to approximately 85°–95° C. and cooling to approximately 40°–60° C. are sufficient. The temperature need be maintained only briefly at the respective levels, 1 to 2 minutes being sufficient. However, the time period may be longer or shorter. The mix with the components for amplification (primers, triphosphates, enzyme) can already be included, or to protect the enzyme, can be added after these denaturing cycles (e.g. as PCR mix).

Addition of the enzyme after denaturation of sample is necessary when isothermal amplification processes such as, TAS, are used in which the enzymes are heat-sensitive. This kind of preparation before actual amplification has already been used in various similar ways in the prior art. For example, Mercier et al., supra, writes that prior repeated thermal denaturing improves the subsequent PCR. This denaturing can be effected simply by some additional cycles during the general amplification reaction when, in any event, the enzymatic process (such as PCR and LCR) requires the denaturing step for DNA amplification. This variation of pretreatment of the sample or reaction mixture is generally applicable to all blood samples.

It is believed that the increase efficiency of amplification due to prior freezing or heating of the samples occurs not because of the neutralization of PCR inhibitors, but because of improved lysis of the cells or viruses. The target nucleic acids, are therefore, liberated before the start of PCR and are thus more readily accessible to the amplification reagents.

The foregoing description of the invention has been made with particular preference for use with PCR as the amplification process for the target nucleic acids and with the use of Taq polymerase as the enzyme. The target-containing sample may be whole blood, plasma or serum. The present invention also contemplates use of polymerases (DNA or RNA) other than Taq, such as one of the thermostable polymerases previously mentioned from *Thermus thermophilus, Thermococcus litoralis* or *Pyrococcus furiosus*. Individual adaptations of the concentration of monovalent and/or bivalent ions in the reaction mixture may be necessary in each case, depending, inter alia, on the enzyme. Particulars about the procedure for certain other enzymes are given infra in Example 6. The range of operation of the enzymes tested is at both high (e.g. ≧10 volume %) and very high blood concentrations (e.g. ≧40 volume %) in the concentration range of approximately 10 to 160 mM of monovalent ions (which was also the concentration described previously with Taq polymerase) and using heparinized samples. In view of the present disclosure, ascertaining the specific limits for other polymerases is a relatively straight forward process for a skilled artisan. Similar considerations as discussed supra. apply to other enzymes, such as, the various reverse transcriptases that are used when the target is RNA and the amplifying process is PCR or TAS.

The following examples are provided by way of illustrating the invention and do not limit the scope of the invention.

The efficient amplification provided by the novel process is demonstrated in Examples 3 and 11, and its reproducibility is demonstrated in Example 4.

Evidence for other possible uses of the novel process is provided by the analysis of very large volumes of blood in Example 5 and of dried blood samples in Example 8. Example 12 provides evidence of the amplification of RNA-target by the PCR process from unpurified serum and plasma samples.

EXAMPLES

General observations regarding PCR conditions used and reported herein:

Unless otherwise specified, all the reactions were performed in a total volume of 50 μl, the so-called "reaction mix". Because of the high sample concentrations therein, correspondingly highly concentrated 10 X PCR buffers containing the necessary salts were used (for the composition of specific PCR buffers, see Point 2 below).

Also, a standard PCR mix containing the nucleoside triphosphates, the primers, buffers and polymerase was used. Unless otherwise specified, the DNA polymerase from Thermus aquaticus was used.

1) The 50 μl reaction mixture was composed as follows:
(a) 4.5 μl of a 10 x concentrated PCR buffer
(b) 5.0 μl of the PCR mix
(c) The required sample volume (μl)
(d) Autoclaved $H_2O$ bidest. q.s. to 50 μl.

2) Composition of PCR buffer (A)
(1) 10 X PCR buffers of the so-called "L" series contained:
— 50 mM of Tricine (pH 8.8) (25° C.)
— 15 mM of MgCl2
— 0.5% Tween 20 (polyoxyethylene-sorbitol-monolaurate)
— and various concentrations of KCl as follows:

Buffer 10 X L0=0 mM KCl
Buffer 10 X L1=100 mM KCl
Buffer 10 X L2=200 mM KCl and so on up to
Buffer 10 X L15=1,500 mM KCl.

(2) 10 X buffer of the LxM series corresponded to the L series but contained 150 mM of $MgCl_2$ instead of 15 mM. For example:

10 X PCR buffers of the LxM series contained:
50 mM of Tricine, pH 8.8 (25° C.),
150 mM of $MgCl_2$
0.5 % Tween 20
and the following different concentrations of KCl:

Buffer 10 X L0=0 mM KCl
Buffer 10 X L1=100 mM KCl
Buffer 10 X L2=200 mM KCl and so on up to
Buffer 10 X L15=1,500 mM KCl.

(3) 10 X T-solution consisted of:
— 15 mM of $MgCl_2$
— 0.5 % Tween 20
(no Tricine, Tris or KCl)

3) Composition of PCR mix (B) for amplification:
0.5 μl of each dNTP (dATP, dCTP, dGTP, dTTP) as 10 mM solution
0.5 μl of the corresponding 10 X PCR buffer
0.5 μl of each primer (50 μM)
1.25 to 2.5 units of DNA polymerase
Water q.s. for a final volume of 5 μl.

Unless otherwise specified, DNA polymerase from *Thermus aquaticus* was used.

Advantageously, the amplification according to Step 1) was performed with 4.5 μl of 10 X PCR buffer (A) and the sample volume (1(c)) was filled up with the autoclaved $H_2O$ (1(d)) to 45 μl. The sample was thermally denatured, when necessary. The 5 μl of the PCR mix, step (b), was added shortly before the start of the PCR. The reaction mixture was covered by two drops, corresponding to 30 to 40 μl, of mineral oil before the denaturing.

4) The thermocycler conditions, per cycle, for amplification of DNA were as follows:

Step 1: 30 sec at 93° C. (separation of the DNA strands)
Step 2: 30 sec at X° C. (hybridization of the primers)
Step 3: 90 sec at 72° C. (polymerase reaction)

20 seconds were interposed between each of the above temperature changes (steps 1–3). A complete cycle, therefore, lasted 3 min and 30 sec. A total of about 35–40 cycles were usually run.

In many experiments the samples were thermally denatured before running PCR. The thermocycler conditions for a denaturing cycle were:

Step 1: 90 sec at 90° C.
Step 2: 90 see at 50° C.

20 cycles were typically run for denaturing, but in some cases, only 5 cycles were run. After the denaturing cycles, the samples were then brought to room temperature, the PCR mix added, and the target nucleic acid was amplified as described.

The following hybridization temperatures (X° C. in Step 2 above) were used with the primers described in Point 5) below:

HLA primer GH26/27: 60° C.

Factor IX primer JR3/JR4: 55° C.

Hepatitis B primer MD 122/MD 123: 50° C.

Rubella primer Ru2/Ru3: 60° C.

5) Sequences of the pCR Primers and Amplified Fragment Size a) HLA DQ alpha gene (242 base pairs) GH26: GTG CTG CAG GTG TAA ACT TGT ACC AG (SEQ ID NO. 1) GH 27: CAC GGA TCC GGT AGC AGC GGT AGA GTT G (SEQ ID NO. 2)

(for primers and sequence See H. Ehrlich et al., PCR Protocols (Acad. Press., 261–271, 1990).

b) Factor IX gene (234 base pairs) JR 3: AGG ACC GGG CAT TCT AAG CAG TTT A (Exon D) (SEQ ID NO. 3) JR 4: CAG TTT CAA CTT GTT TCA GAG GGA A (SEQ ID NO. 4)

(for primers and sequence see J. Reiss et al., Blut 60:31–36, 1990).

c) Hepatitis B (151 base pairs) MD 122: CTC TCA ATF TTC TAG GGG GA (SEQ ID NO. 5) MD 123: AGC AGC AGG ATG AAG AGG AA(SEQ ID NO. 6)

These primers amplify a 153 bp long fragment of the hepatitis B virus. Primer No. MD122 is at bp 267–286, No. 123 at Bp 401–420 of the HBV genome (sequence numbering according to H. Okamoto et al., J. Gen. Virol. 67:2305–2314, 1986).

d) Rubella (321 base pairs) Ru 2: TGC TTT GCC CCA TGG GAC CTC GAG (bp 1990–2013) (SEQ ID NO. 7) Ru 3: GGC GAA CAC GCT CAT CAC GGT (bp 2290–2310) (SEQ ID NO. 8)

(for sequence of primers see Eggerding F. et al., J. Clin. Microb. 29:945– 952, 1991).

6) DNA and RNA polymerases used a) Taq polymerase from *Thermus aquaticus*: Super Taq (Stehelin, Switzerland) as 5 units/µl in 20 mM of Tris (pH 8.0), 1 mM of EDTA, 1 mM of DTT and 50% glycerin.

b) DNA polymerase from *Thermococcus litoralis*: Vent (Trademark of New England Biolabs), 1000 units/ml in 100 mM of KCl, 0.1 mM of EDTA, 10 mM of Tris-HCl (pH 7.4), 1 mM of DTT, 0.1% of Triton-X-100, 100 µg/ml of BSA and 50% glycerol.

c) Pfu DNA polymerase from *Pyrococcus furiosus* (Stratagen) 2500 units/ml in 50 mM of Tris HCl (pH 8.2), 1 mM of DTT, 0.1 mm of EDTA, 0.1% of Tween-20, 0.1% of NP-40 and 50% of glycerol.

d) rTth DNA polymerase from *Thermus thermophilus* (Perkin Elmer), 2500 units/ml in 100 mM of KCl, 20 mM of TRIS-HCl (pH 8.0), 0.1 mM of EDTA, 1 mM of DTT, 0.5% of Tween 20 and 50% glycerol.

e) Reverse transcriptase (from Moloney Murine Leukemia Virus (BRL)), 200 units in 20 mM of TRIS-HCl, 1 mM of DTT, 0.01% of NP-40, 0.1 mM of EDTA, 0.1 M of NaCl and 50% glycerol.

7) Analysis of the amplification products

After amplification the blood samples were centrifuged at 12,000 g for 5 minutes. Thereafter, 5–7 µl of the residue were applied to an agarose gel. Samples containing ≧40 volume % of whole blood are diluted with 30 µl of water before centrifuging. The ampiicons are identified by staining with ethidium bromide after electrophoresis on 2% agarose gel which is not an ampiicon-sensitive identification procedure. Thus weak PCR results were evaluated negative.

EXAMPLE 1

PCR Dependence Upon KCl

Initial experiments with EDTA-treated blood show that after denaturing, it is possible to amplify chromosomal DNA fragments in a reaction mix having 10% blood by volume.

The tests for determining the critical KCl concentrations for the Taq polymerase were repeated with the PCR instead of a linear radioactive incorporation assay (see Chapter 2: Taq DNA Polymerase by D. Gelfand; PCR Technology, Stockton Press 1989; Editor Henry Ehrlich). Purified DNA or 20 volume % denatured EDTA-treated blood was used as substrate.

The fragment of the HLA gene DQalpha was amplified with 10 µl of denatured EDTA-treated blood or 20 ng of purified DNA at KCl concentrations between 0.0 mM and 150 mM in the PCR buffer. The other components of the buffer remained constant. The blood samples were denatured in the thermocycler in 20 cycles before the PCR. The amplicon synthesis was performed in 35 cycles. 7 µl of the product was then separated out electrophoretically on agarose gel and stained with ethidium bromide. The quantity of the 242 bp long amplicon of the HLA gene DQalpha was measured and it was found that the concentration of monovalent ions is one of the decisive factors for the efficiency and specificity of synthesis by Taq polymerase. The following KCl values reflect the concentration of the salt in the PCR buffer but do not reflect the total KCl in the reaction mix inasmuch as the sample is disregarded.

In the case of purified DNA, the amplicon could be detected at concentrations of KCl of 10 mM to 150 mM. In the case of 20 volume % blood, detection was possible at 0 mM to 110 mM of KCl. Maximum synthesis occurred for purified DNA at approximately 70 to 80 mM of KCl and for 20 volume % blood, between 0 and 50 mM KCl.

At concentrations less than or equal to 40 mM of KCl in the buffer (with purified DNA), the Taq polymerase tends to synthesize unspecific sequences of different length which show up as a DNA smear on the agarose gel. This background of unspecific sequences was weak at 40 mM KCl. The background was very noticeable at ≦30 mM KCl in the buffer and it clearly hampered the desired specific amplification.

This unspecific DNA synthesis ("background") was visible only when purified DNA was used as the substrate. At 20 volume % of blood, the salt concentration of the blood solution was sufficient to ensure the specificity of the reaction in all the KCl concentrations tested in which any amplification could still be observed. Excessive concentrations of KCl reduced amplicon synthesis and 150 mM KCl in 20 volume % of blood, completely inhibited PCR amplification.

Specific synthesis in 20 volume % of blood was possible not only in the absence of KCl in the PCR buffer but also in the absence of tricin or Tris (Table 1). In this case, the PCR buffer was replaced with solution T (above) containing only MgCl$_2$ and Tween 20 (for the composition of the solution see "General Observations on the PCR Conditions"). Consequently, if the blood concentration in the PCR mixture is high enough, the buffer capacity and the salt content of monovalent ions of the sample suffice to produce specific DNA synthesis.

TABLE 1

| | PCR dependence upon KCl | | | | | | | |
|---|---|---|---|---|---|---|---|---|
| KCl (mM) | T | L0 | L1 | L3 | L5 | L7 | L9 | L11 L15 |
| Buffers | 0.0, | 0.0, | 10, | 30, | 50, | 70, | 90, | 110, 150 |
| Substrate: purified DNA | NT | NT | +/U | +/U | ++ | ++ | ++ | ++ + |
| EDTA-treated blood | ++ | ++ | ++ | ++ | ++ | ++ | ++ | + − |

++: very good or good amplification
+: weak amplification
−: no visible amplification
U: unspecific DNA synthesis
NT: not tested

EXAMPLE 2

PCR in the presence of denatured blood or blood treated with heparin, EDTA or citrate This example tests the efficiency of amplification in the presence of 5–50 volume % denatured blood at different salt concentrations. The amplification of the DQalpha sequence with Taq polymerase was again determined.

The specified concentrations of blood of different origin were denatured in 50 μl reactions with different salt concentration. Thereafter the DQalpha-specific fragment in each sample was PCR amplified for 40 cycles. The PCR was performed in the presence of 2.5 to 25 μl of blood, corresponding to about 5–50 volume % of the total reaction volume. The amplicons were identified by ethidium bromide after electrophoresis of 7 μl of residue on agarose gel. The complete composition of the PCR buffers was as set forth above in Example 1. The final Mg2+ concentration of the LxM buffers in the assay was 15 instead of the usual 1.5 mM in buffers of the L series. The results are summarized in Table 2.

a) Heparinized blood

Heparin-treated blood was found to have the least reaction sensitivity to different KCl concentrations. The specific DNA amplification was achieved in the presence of 5–50 volume % of blood by the use of the L5 buffer and in the presence of 10–50 volume % of blood (solution T, 2)(3) above). At 40 volume % and 50 volume % of blood, more amplicon was found after treatment with T solution than after treatment with the L5 buffer. This indicates that amplification was more efficient in the absence of monovalent ions. There was no disturbing background (undesired synthesis) in any of the amplifications.

b) EDTA-Treated blood

The affect of KCl content on the activity of Taq polymerase in PCR was more clearly noted with EDTA-treated blood. Amplification of specific DNA sequences of 5–30 volume % of blood was possible in L5 buffer and of 10–50 volume % of blood in the T solution. Unspecific DNA synthesis occurs in the T solution at levels below 20 volume % of blood. At 5 volume % of blood, only unspecific background synthesis occurs and no specific synthesis could be detected.

The synthesis maximum for the DQalpha amplicon is approximately 10 volume % with the L5 buffer and approximately 30 volume % of blood with the T solution.

c) Citrated blood

Taq polymerase behaves quite differently in the presence of citrated blood than in the presence of EDTA-or heparin-treated blood. No synthesis at all was possible with either the L0 buffer or the T solution. With the L5 buffer, amplification in 5 and 10 volume % of blood was possible and, very weakly, in 20 volume % of denatured blood. Synthesis in relatively large quantities of blood was possible when high MgCl$_2$ and KCl concentrations were used. In the L10M buffer containing 100 mM of KCl and 15 mM of MgCl$_2$ the amplicon was formed in the presence of 5–50 volume % of blood. In the L5M buffer, amplification was observed in 20–50 volume % of blood. In the L0M solution, amplification was noted at 40 and 50 volume % of citrated blood. A very strong undesirable background synthesis was noted with the two latter buffers in the presence of relatively small quantities of blood.

This example shows that specific DNA amplification by PCR was possible with all 3 of the above commonly used anticoagulants in the presence of 5–50 volume % of denatured blood with Taq polymerase and appropriate buffers. It was found that the amplification reaction from heparin-treated blood was the least sensitive to different concentrations of monovalent ions and also provided the most specific synthesis.

TABLE 2

PCR in the presence of 5–50 volume % of denaturated blood treated with heparin, EDTA or citrate

| | Concentration of blood in PCR Mix (vol. %) | | | | | |
|---|---|---|---|---|---|---|
| | 5% | 10% | 20% | 30% | 40% | 50% |
| Heparin-Treated Blood | | | | | | |
| 0 mM KCl (T) | − | ++ | ++ | ++ | ++ | ++ |
| 50 mM KCl (L5) | ++ | ++ | ++ | ++ | ++ | ++ |
| EDTA-Treated blood | | | | | | |
| 0 mM KCl (T) | −/U | +/U | ++ | ++ | ++ | + |
| 50 mM KCl (L5) | ++ | ++ | ++ | + | − | − |
| Citrated blood | | | | | | |
| 0 mM KCl (T) | − | − | − | − | − | − |
| 0 mM KCl; 15 mM MgCl$_2$ (L0M) | −/U | −/U | −/U | +/U | ++/U | ++/U |
| 50 mM KCl (L5) | ++ | ++ | + | − | − | − |
| 50 mM KCl; 15 mM MgCl$_2$ (L5M) | −/U | +U | ++/U | ++ | ++ | ++ |
| 100 mM KCl (L10) | ++ | ++ | − | − | − | − |
| 100 mM KCl; 15 mM MgCl$_2$ (L10M) | ++ | ++ | ++ | ++ | ++ | + |
| 150 mM KCl; 15 mM MgCl$_2$ (L15M) | ++ | ++ | ++ | + | + | − |

T: without the normal 5.0 mM of Tricine
−: no specific amplification visible
+: barely detectable aplicon

TABLE 2-continued

PCR in the presence of 5–50 volume % of denaturated blood treated with heparin, EDTA or citrate

| | Concentration of blood in PCR Mix (vol. %) | | | | | |
|---|---|---|---|---|---|---|
| | 5% | 10% | 20% | 30% | 40% | 50% |

++: good to very good detection of amplicon
U: unspecific DNA synthesis

Table 2 shows that the L10M buffer, giving a concentration of 10 mM of KCl and 15 mM of $MgCl_2$ in the reaction mixture, is suitable for DNA-PCR amplification from titrated blood.

The necessary $MgCl_2$ concentration is defined more accurately in Example 2A.

EXAMPLE 2A

Optimization of the $MgCl_2$ concentration for PCR in citrated blood

HLA DQalpha sequences were amplified from 10 μl and 25 μl, respectively, of citrated blood of two people (A and B) in different magnesium concentrations. The reactions contained 0.05% of Tween, 5 mM of Tricine (pH 8.8) and 50 mM of KCl, with a 20 volume % of citrated blood. Also tested were solutions with and 100 mM of KCl with a 50 volume % concentration of citrated blood (Samples 1 to 7), and 80 mM of KCl with 50 volume % of citrated blood (samples 8 to 11). A total of 40 amplification cycles were performed after denaturing the DNA in the blood sample. In other respects, the performance of the test and evaluation were similar to those described in Example 2 above. The results are shown in Table 3 below.

TABLE 3

| Concentration of citrated blood in PCR Mix (vol. %) | | 20% | | 50% | |
|---|---|---|---|---|---|
| Sample | $MgCl_2$ (mM) | A | B | A | B |
| 1 | 1.5 | − | − | NT | NT |
| 2 | 2.5 | − | − | − | − |
| 3 | 3.5 | + | + | − | − |
| 4 | 4.5 | ++ | ++ | − | − |
| 5 | 5.5 | ++ | ++ | − | − |
| 6 | 6.5 | ++ | ++ | + | + |
| 7 | 7.5 | ++ | ++ | ++ | + |
| 8 | 11.5 | ++ | ++ | ++ | ++ |
| 9 | 15.5 | ++ | ++ | ++ | + |
| 10 | 21.5 | ++ | ++ | ++ | + |
| 11 | 41.5 | − | − | + | + |

The symbols used in Table 3 have the same meaning as in Table 1 above.

The optimum $MgCl_2$ concentration was found to be between 4.5 and 21.5 mM, depending on the origin and size of the samples.

EXAMPLE 3

Determination of the efficiency of PCR amplification of DNA samples in whole blood 1 microlitre of blood of an adult contains 4000 to 9000 leucocytes (on average 5000). As shown in Example 2, 20 ng of purified DNA, corresponding approximately to the genomic material of 3000 cells (6.8 pg of DNA/diploid cell), are sufficient to synthesize a clearly detectable quantity of amplicon using PCR. If there is a quantitative lysis of the leucocytes, so that the genomic DNA is first converted into a substrate suitable for PCR, and if there is no inhibition of the amplification reaction by components of the unpurified blood sample, 1 μl of whole blood should therefore be sufficient for an efficient amplicon synthesis.

An experiment to determine the efficiency of the claimed novel sample processing for PCR was therefore devised as described herein. Human EDTA-treated blood was diluted with EDTA-treated sheep's blood whose DNA does not cross-react with the HLA primers GH26 and GH27. In this experiment, 10 μl each of frozen, denatured EDTA-treated human and sheep's blood were used both undiluted as well as at varying dilutions, in a PCR assay as previously described. Amplification was carried out in L2 buffer for 40 cycles with the primer pair GH26 and GH27, which is specific for the human HLA gene DQalpha. The results are summarized in Table 4 below. It was found that at 40 amplification cycles, as few as 50 human cells were sufficient to yield a detectable amplicon band.

TABLE 4

| Sample (Dilution factor of human blood; sheep's blood) | Human leucocytes per PCR mix | Amplicon synthesis |
|---|---|---|
| All Human blood | 50,000 | ++ |
| 1:10 | 5,000 | ++ |
| 1:100 | 500 | ++ |
| $1:10^3$ | 50 | + |
| $1:10^4$ | 5 | − |
| $1:10^5$ | 0.5 | − |
| All Sheep's blood | − | − |

The above symbols have the same meaning as in Table 1.

EXAMPLE 4

PCR in 20 volume % and 40 volume % of denatured blood of different persons

The process for amplifying a DNA fragment by PCR in 20 or 40 volume % blood was checked in a small group of different samples. The DNA from 10 EDTA, 5 heparin and 4 citrate-treated blood samples were efficiently amplified with the DQalpha specific PCR primers in the optimized conditions. The amplification was carried out for 40 cycles in 50 μl reactions from 10 and 20 μl of denatured blood, respectively, of the various persons. PCR buffers were L0 for the EDTA and heparin-treated blood samples (5 mM of Tricine (pH 8.8), 1.5 mM of $MgCl_2$ and 0.05% of Tween), and L10 (5 mM of Tricine (pH 8.8), 100 mM of KCl, 15 mM of $MgCl_2$, 0.05% of Tween) for the citrated blood. The results are given in Table 5 below. All the samples were positive. Taq polymerase was not noticeably inhibited in any of the assays and there was no disturbing amplification of unspecific sequences.

TABLE 5

PCR in 20 and 40 volume % of denatured blood of different persons

| Concentrations of blood in the PCR Mix (Volume %) | 20% | 40% |
|---|---|---|
| a) EDTA-treated blood | | |
| Person 1 | ++ | ++ |
| Person 2 | ++ | ++ |
| Person 3 | ++ | ++ |
| Person 4 | ++ | ++ |

TABLE 5-continued

PCR in 20 and 40 volume % of denatured blood of different persons

| Concentrations of blood in the PCR Mix (Volume %) | 20% | 40% |
|---|---|---|
| Person 5 | ++ | ++ |
| Person 6 | ++ | ++ |
| Person 7 | ++ | ++ |
| Person 8 | ++ | ++ |
| Person 9 | ++ | ++ |
| Person 10 | ++ | ++ |
| b) Heparin-Treated blood | | |
| Person 11 | ++ | ++ |
| Person 12 | ++ | ++ |
| Person 13 | ++ | ++ |
| Person 14 | ++ | ++ |
| Person 15 | ++ | ++ |
| c) Citrated blood | | |
| Person 16 | ++ | ++ |
| Person 17 | ++ | ++ |
| Person 18 | ++ | ++ |
| Person 19 | ++ | ++ |

++: Very clearly visible quantity of amplicons

EXAMPLE 5

PCR in large-scale reactions

Of particular interest in the identification of infectious microorganisms, which are often present in the blood in a very small concentration, is the maximum foreign DNA/RNA quantity in which a particular sequence can be amplified specifically and efficiently in a PCR assay.

In blood, a distinction is made between nucleus-free or DNA-free red blood corpuscles and nucleus-containing white blood corpuscles or leucocytes, of which the mononuclear blood cells (MZ) make up about one-third. The average contents of 1 μl of adult blood is approximately 5,000 leucocytes, or 100,000 MZ in 60 μl of blood.

For the identification of, for example, HIV-DNA, the PCR is conventionally performed in 100 μl reaction mix volumes with about 50,000 to 100,000 MZ. This corresponds to about 340 to 680 ng of DNA (given a content of 6.8 pg per diploid cell). The upper limit of approximately 1 μl of DNA per mix is usually not greatly exceeded because the specific amplicon synthesis decreases if the concentration of foreign DNA is excessive (M. Abbott et al., J. Infect. Disease 158:1158–1169, 1988).

Conditions have been found for amplifying sequences specifically in the presence of 400,000 or more MZ.

One simple way of increasing the sample volume per PCR mix is to perform large-scale PCR, the reaction volume being increased from 50– 100 μl to about 500 μl.

Experiments with 500 μl large-scale reactions were carried out with the same reaction vessels and same thermocycler as were used for the 50 μl mixes. The proportions of the reaction components were not altered.

Composition of the PCR mix:

5 μl each of dATP, dCTP, dGTP + dTTP (10 mM solutions)

5 μl of the corresponding 10 X PCR buffers

5 μl for each primer (50 gM)

2.5 units of the Taq polymerase (2.5 μl)

Reaction mix:

45 μl of the 10 X PCR buffer

100–400 μl of sample $H_2O$ q.s. for 467.5 μl.

The samples were denatured in 20 cycles under the conditions specified in Example 1. Thereafter 32.5 μl of PCR mix was added to each of the reactions.

The thermocycler program used to identify DQalpha in large-scale reactions was as follows:

| Step 1 | 3 min at 93° C. |
|---|---|
| Step 2 | 3 min at 60° C. |
| Step 3 | 3 min at 72° C. |

A 20 seconds pause was allowed between each temperature change. A cycle therefore lasted 10 minutes and the number of cycles was 40.

Using the large scale procedure, a 242 bp fragment from the HLA DQalpha gene was amplified. The PCR was performed in 500 μl reaction volume and contained between 100 to 400 μl of denatured heparin-treated blood. In contrast to the normal 50 μl mixes, in some of the large scale reactions 80 μl of oil were used instead of 30–40 μl. In other respects, the 50 μl and 500 μl PCR mixes had the same relative proportions of the various reaction components.

Table 6 below summarizes the results of the amplification of 200 μl of heparin-treated blood from 5 different donors. An efficient and specific synthesis of the DQalpha amplicon was achieved with each sample.

At 40 volume % concentration of sample in the 500 μl PCR large-scale reaction the, 200 μl of blood contained approximately $1 \times 10^6$ leucocytes with about 6.8 μg of DNA. Of these, approximately one-third are mononuclear cells.

Larger quantities of blood, viz. 250–400 μl (which is equal to 50–80 volume %), were used experimentally with heparinized blood samples and, as is shown below in Table 6(b), were successfully amplified.

TABLE 6

PCR in large-scale reactions
(a) PCR in T-solution: 200 μl of heparinized blood from five different persons
Concentration of heparinized blood in large-scale PCR = 40 volume %

| Blood donor 1 | ++ |
|---|---|
| Blood donor 2 | ++ |
| Blood donor 3 | ++ |
| Blood donor 4 | ++ |
| Blood donor 5 | ++ |

(b) PCR in L0 buffer: 100 to 400 μl of heparinized blood
Concentration of heparinized blood in large-scale PCR

| | (Volume %) | | | |
|---|---|---|---|---|
| | 20% | 40% | 60% | 80% |
| Donor 1 | ++ | ++ | ++ | ++ |

The symbols used in Table 6 have the same meaning as in Table 1 above.

EXAMPLE 6

Synthesis of the DQalpha amplicon from denatured whole blood with heat-stable DNA polymerases from three kinds Of bacteria other than *Thermus aquaticus*

In all the previous examples DNA was amplified from denatured whole blood with Taq DNA polymerase. Amplification of the DQalpha fragment was therefore tested for three DNA polymerases of different origin. Whereas the Taq polymerase is isolated from *Thermus aquaticus*, the Pfu polymerase is from *Pyrococcus furiosus*. (Stratagene), the VentR polymerase is from *Thermococcus litoralis* (New England Biolabs), and the Tth polymerase is from *Thermus thermophilus* (Perkin-Elmer).

10 volume % and 40 volume %, respectively, of heparinized blood were denatured in the buffers accompanying each enzyme. Thereafter, the 242 bp fragment of the HLA gene was amplified. Conditions in which the amplicon formed efficiently in the presence of 10 volume % or 40 volume % whole blood were ascertained for all three enzymes as follows: "Hot start" amplification of 5 or 20 μl of denatured, heparinized blood in the enzyme manufacturer's PCR buffer for Pfu and Vent, and in L9 for rTth, reaction volume of 50 μl. Negative control was performed by amplification without blood with Pfu, i.e. 5 μl of heparin blood being replaced by 5 μl of H₂O. The "Hot start" amplification was performed by heating the blood to 60° C. after denaturing and after the addition of the PCR mix (without polymerase). The enzyme was added after 10 minutes at this temperature and the PCR carried out for 40 cycles.

Composition of the 10 X buffers used in Table 7

Buffer 1: 200 mM Tris, pH 8.8 100 mM KCl 60 mM (NH$_4$)$_2$SO$_4$ 20 mM MgCl$_2$ 1% Triton X- 100 1 mg/ml nuclease free BSA Buffer 200 mM Tris, pH 8.8 100 mM KCl 60 mM (NH$_4$)$_2$SO$_4$ 15 mM MgCl$_2$ 1% Triton X-100

Vent: 200 mM Tris, pH 8.8

Buffer 100 mM KCl 100 mM (NH$_4$)$_2$SO$_4$ 20 mM MgCl$_2$ 1% Triton X-100

The results in Table 7 show that DNA that was denatured, but not purified, in blood samples can be amplified with the four different DNA polymerases, and that the amplification is not dependent upon the specific properties of Taq polymerase.

TABLE 7

PCR amplification of DNA from denatured, whole blood using three different heat-stable DNA polymerases

| Polymerase | Heparinized Blood | | Buffer | PCR |
| --- | --- | --- | --- | --- |
|  | 5 m | 20 ml |  |  |
| Pfu | + |  | 1 | ++ |
| Pfu |  | + | 1 | − |
| Pfu | + |  | 2 | + |
| Pfu |  | + | 2 | − |
| rTth | + |  | L9 | ++ |
| rTth |  | + | L9 | ++ |
| Vent | + |  | Vent (-BSA) | ++ |
| Vent |  | + | Vent (-BSA) | ++ |
| Control (Pfv) | − | − | 1 | − |

The symbols above have the same meaning as in Table 1.

Pfu is Polymerase of Pyrococcus rTth is Polymerase of *Thermus thermophilus*

Vent is Polymerase of *Thermococcus litoralis*

EXAMPLE 7

Amplification of a DNA sequence from Factor IX, the hereditary factor for blood

All the examples given are based on identifying the 242 bp amplicon from the HLA DQalpha gene. Amplification from whole blood was accomplished for the 234 bp long fragment from the gene for blood factor IX.

Defects in factor IX, an X-chromosomal and recessive gene, lead to a blood disorder known as haemophilia B (or Christmas disease). The sequence of this hereditary factor, which is a single copy gene, is known in the art (See Yoshitake et al., Biochemistry 24:3736–3750 (1985)). The sequence of the primers JR3 and JR4 for the amplification of the 234 bp fragment from the Exon d was taken from J. Reiss et al. (Blut 60:31–36 (1990)).

10 μl and 20 μl, respectively, of heparinized blood of five different people were denatured in buffer L5 and factor IX DNA was amplified with primers JR3 and JR4 in 50 μl of reaction volume (see Table 8). The expected amplicon magnitude of 234 Bp was detected on agarose gel with all the tested blood samples. The expected DNA band was less intensive at 20 μl of blood and some unspecific weak secondary bands appeared in addition to the main band. Except for approximate determination of the annealing temperature for JR3/JR4 with purified DNA, no further optimization of the assay was made.

The denatured, whole blood was amplified in 37 cycles each of which consisted of 30 sec at 93° C., 30 sec at 55° C. and 90 see at 72° C. Table 8 below summarizes the results.

TABLE 8

Amplification of a DNA seguence from the gene of blood factor IX

| Heparinized blood | | | Synthesis of 234 Bp |
| --- | --- | --- | --- |
| 5 μl | 20 μl | Donors | amplicon |
| + |  | 1 | ++ |
| + |  | 2 | ++ |
| + |  | 3 | ++ |
| + |  | 4 | ++ |
| + |  | 5 | ++ |
|  | + | 1 | + |
|  | + | 2 | ++ |
|  | + | 3 | ++ |
|  | + | 4 | ++ |
|  | + | 5 | ++ |
| negative control |  |  | − |

The symbols above have the same meaning as in Table 1.

EXAMPLE 8

Amplification from dried blood samples

Collecting blood samples in remote places, often with unsatisfactory facilities, and transportation thereof may present some difficulties. A simple solution is to drip blood samples on filter paper and preserve the dried samples. Samples of this kind, known as Guthrie spots, have a long life for purposes of use as starting material for immunological and virological tests (NCCLS Document LA4-A2, July 1992, 2nd edition).

Blood samples dried on filters have already been used in PCR assays. The DNA from the dried blood was eluted and partly purified and a specific sequence amplified (See I. Huang et al, Hum. Genet. 84:129–131 (1990), and Nelson et al, The Lancet 336:1451–1452 (1990)).

For the direct amplification of blood from Guthrie spots, 5 μl of EDTA blood and heparin blood were dripped on 3 different filter supports, dried at 37° C. for 2 hours, then cut out and the filter piece was added to a 50 μl PCR assay using L5 buffer and amplified after 20 denaturing cycles. The 242 bp amplicon from the DQalpha gene was detectable. As Table 9 shows, all the tested samples with the various filters gave a positive result after 40 amplification cycles.

TABLE 9

PCR Amplification of Blood Samples on filter pieces containing 5 µl of blood

| Filter | Blood treated with | PCR |
|---|---|---|
| Nitrocellulose (SS BA85/20; 45 µM) | EDTA | ++ |
| Nitrocellulose (SS BA85/20; 45 µM) | Heparin | ++ |
| Filter paper SS (for dotblots) | EDTA | ++ |
| Filter paper SS (for dotblots) | Heparin | ++ |
| Nylon membrane (Pall) | EDTA | + |
| Nylon membrane (Pall) | Heparin | ++ |

The symbols above have the same significance as in Table 1.

EXAMPLE 9

Amplification from fresh blood

All the examples described were performed with frozen blood from blood donors of the Basle Cantonal Hospital, whereby aliquots of the blood had been prepared two days after collection and stored at −70° C. It will be shown in a further test that it is simple to use fresh blood — i.e., blood not previously frozen but also mixed with anticoagulants — for the PCR assay.

The test conditions were as follows:

Amplification by PCR of 10 µl of each fresh blood, heparinized blood and citrated blood (each of which had been stored for 2 hours), and EDTA-treated blood (which had been stored for 24 hours at room temperature) was performed for 43 cycles. If indicated 30 minutes freezing at −70° C. was given. The 10 µl of blood were increased to 45 µl with $H_2O$, 5 gl of L3 buffer (for heparin and EDTA blood) and 5 µl of L10M buffer for citrated blood, were indicated thermally denatured as stated above, then the PCR mix (5 µl) was added and the PCR started.

Table 10 below summarizes the results of this example.

It was found that PCR was effective on heparinized blood and citrated blood samples without any additional denaturing or previous freezing steps. Cellular DNA from EDTA-treated blood could not be amplified directly. A prior freezing step was necessary. In the case of heparinized blood and citrated blood, no difference was ascertained between the different forms of sample preparation, viz. freezing, freezing and denaturing (five cycles), or freezing and 20 denaturing cycles (the result of the latter form of preparation is not shown). However, with fresh EDTA-treated blood, a stronger signal was observed after 20 pre-PCR denaturing cycles than after only 5 cycles. Also, after storage of the heparinized blood and citrated blood for 5 days at room temperature, PCR amplification showed no difference between samples not having been subjected to preparation or freezing, with and without denaturing, whereas a noticeable difference remained in the case of EDTA-treated blood (result not shown).

TABLE 10

Dependence of PCR with fresh, denatured or fresh, non-denatured whole blood upon added Anticoagulants

| Pre-PCR treatment of sample | | − = room-temperature + = freezing (−70° C.) | 5 denaturing cycles (90°/50° C.) | PCR results 242 bp-amplicon HLA-DQalpha |
|---|---|---|---|---|
| A) | EDTA-Treated blood | | | |
| | A | − | − | − |
| | B | − | − | − |
| | A | + | − | ++ |
| | B | + | − | ++ |
| | A | + | + | ++ |
| | B | + | + | ++ |
| B) | Heparin-Treated blood | | | |
| | A | − | − | + |
| | B | − | − | + |
| | A | + | − | ++ |
| | B | + | − | ++ |
| | A | + | + | ++ |
| | B | + | + | ++ |
| C) | Citrated blood | | | |
| | A | − | − | + |
| | B | − | − | + |
| | A | + | − | ++ |
| | B | + | − | ++ |
| | A | + | + | ++ |
| | B | + | + | ++ |
| D) | Control | | | |
| | C | + | + | − |
| | D | + | + | ++ |

For PCR results: — no signal; +, ++ signal of increasing strength; Control: C is EDTA-treated sheep's blood, D is heparinized blood stored at 70° C. for six months.

EXAMPLE 10

PCR in the presence of denatured serum or plasma

For the screening of blood samples for RNA viruses such as, for example, hepatitis C virus or HIV, it would be advantageous technologically if a PCR assay of infectious pathogens of this kind could be done directly with unpurified blood (or serum or plasma). This would eliminate tedious sample preparation of the RNA, reduce the risk of contamination of the samples and facilitate automation of sample screening.

A buffer giving efficient amplification of 20 ng of human DNA in 10 volume % and 40 volume %, respectively, of denatured serum or EDTA-, heparin-, or citrate-treated plasma was sought. The DQalpha amplicon was amplified with all four kinds of samples and conditions according to the present as is shown on Table 11. It was found that in the case of the 40 volume % sample, higher magnesium concentrations were necessary in the PCR reaction mix than in the case of the 10 volume % sample. The reason for this in the case of EDTA-treated blood is that, generally, equimolar quantities of magnesium are bound by EDTA- i.e., 1 mM of EDTA binds 1 mM of magnesium. Only the free $Mg^{2+}$ concentration has an effect on amplification. The preferred $Mg^{2+}$ concentration for EDTA-treated blood is somewhere between at least 1.4 mM (10 volume % of EDTA-treated blood) and approximately 5.0 mM (80 volume % of EDTA-treated blood).

The amplification was performed in a 50 μl reaction volume of 20 ng of human DNA in 5 μl (A) or 20 μl (B) of denatured plasma from a donor whose blood was prepared differently in each case. The plasma was made up to 45 μl with H$_2$O, 5 μl of 10 X buffer and 1 μl of DNA and denatured in 20 cycles. Then, 5 μl of this solution were added to the PCR mix and the DQalpha fragment amplified for 40 cycles. The results are given below in Table 11.

TABLE 11

PCR in the presence of 10 volume % (A) and 40 volume % (B), respectively, of denatured plasma or serum

| | | Plasma treated with | | | |
|---|---|---|---|---|---|
| | Buffers | Citrate | EDTA | Heparin | Serum |
| (A) | L5 | + | − | ++ | ++ |
| | L9 | − | + | ++ | ++ |
| (B) | L5M | ++ | + | + | + |
| | L10M | − | + | − | + |

The symbols above have the meaning as in Table 1.

EXAMPLE 11

Amplification of HBV from Serum

DNA surrounded by proteins — in this case viral hepatitis B DNA — was efficiently detected after amplification by means of an appropriate buffer according to Example 10 for the amplification of purified DNA in the presence of serum. To this end, a serum having an HBV count of 1.5 ×10$^7$ HB viruses per microlitre (determination of count by means of the Abbott test No. 2022: Kit for vital HBV-DNA detection and quantification) after different dilution, was amplified in control serum with HBV specific primers MD122 and MD123. 10 μl of serum were denatured in 50 μl of reaction volume with L5 buffer and after addition of the PCR mix, amplified for 40 cycles. The products were analyzed on agarose gel. The results are summarized below in Table 12.

TABLE 12

| Sample | No. of HBV genomes per PCR assay | Amplicon synthesis |
|---|---|---|
| 1 | 1.5 × 10$^6$ | ++ |
| 2 | 1.5 × 10$^5$ | ++ |
| 3 | 1.5 × 10$^4$ | ++ |
| 4 | 1,500 | + |
| 5 | 150 | − |
| 6 | 15 | − |
| 7 | 0 (Control serum) | − |

The symbols above have the same meaning as in Table 1.

With this process, samples containing 1,500 or more HBV DNA molecules yielded a visible amplicon band after staining of the amplified DNA by ethidium bromide in the agarose gel. The PCR assay can be much more sensitive if a sensitive identification process is used, such as for example, hybridization of the amplicon with a radioactively labeled probe.

EXAMPLE 12

RNA-PCR in the presence of non-denatured and unpurified Serum or plasma

Rubella was chosen as the substrate for the RNA-PCR amplification. Rubella is a virus of the family of the Toga viruses which includes hepatitis C agent. The genome is a single-strand RNA of over 10 kb. Rubella contains no reverse transcriptase. Unlike HIV, at no stage of its amplification does it consist of DNA. Preparations of the Rubella virus therefore contain no Rubella DNA.

10 μl of EDTA-treated plasma or serum and 20 volume % of the end volume of the reaction mixture were introduced, without denaturing, into an RNA-PCR mix. The Rubella virus preparation was used directly without previous purification in the reverse transcriptase assay (RTA) and the eDNA obtained was used as starting substrate for a Rubella-specific PCR. The RNase inhibiting substance in the RTA is important in this process.

Deep-frozen serum and plasma were defrosted and 10 μl of each were diluted to 46 μl with Mix 1 (described below). The RNasin and the RNase block were replaced by H$_2$O in Mix 1 for reactions 2 and 4. The reaction Mixes were covered with 30–40 μl of mineral oil and incubated at 42° C. for 30 minutes. After heating to 95° C. for 2 minutes, 4 μl of Mix 2 (described below) were added and the DNA amplified for 40 cycles. The products were analyzed on agarose gel. The results are summarized in Table 13 below.

Mix 1: −5 μl of L8 buffer —20 μl of 50% glycerine —1 μl of random hexamer (1.65 μg/μl) —0.5 μl of RNasin (40 units/μl) (Serva) —0.5 μl of RNase block (1 unit/μl) (Stratagene) —0.1 μl of each of dATP, dCTP, dGTP and TTP (100 μM solutions) —0.8 μl of reverse transcriptase (MMLV; 200 units/μl) —6.8 μl of H$_2$O cell —1 μl of Rubella virus M-33 (unpurified frozen cell residue, ATCC Order No. VR-315)

Mix 2: −25 pmol each of Rubella Primer Ru2 and Ru3 (see General Observations on PCR Conditions) —0.4 gl of L8 buffer —1.25 units of Taq polymerase —H$_2$O q.s. for 4 μl

TABLE 13

| | Serum 10 ml | Plasma 10 ml | Rubella Virus | RNasein and RNase block | PCR |
|---|---|---|---|---|---|
| 1 | − | + | + | + | ++ |
| 2 | − | + | + | − | − |
| 3 | + | − | + | + | ++ |
| 4 | + | − | + | − | − |

The symbols above have the same meaning as in Table 1.

This Example shows that viral RNA can be detected by PCR in non-denatured serum or plasma.

I claim:

1. A method for enzymatic amplification of target nucleic acid sequences in a blood sample treated with an anticoagulant, carried out in an amplification reaction mixture, said blood sample comprising at least five volume per cent of said reaction mixture, said method comprising:
   (a) determining the concentration of monovalent ions and bivalent ions in said anticoagulant-treated blood sample;
   (b) adjusting the monovalent ion concentration in said reaction mixture to a range of 10–200 mM;
   (c) if bivalent ions are present in said anticoagulant-treated blood sample, adjusting the bivalent ion concentration in the reaction mixture to a range of 1.4–40 mM; and
   (d) amplifying the target nucleic acid sequences in said blood sample.

2. The method of claim 1, wherein the blood sample is treated with an anticoagulant selected from the group consisting of heparin, ethylenediaminetetraacetic acid (EDTA) and citrate.

3. The method of claim 1, wherein the monovalent ions are $Na^+$ and $K^+$.

4. The method of claim 1 wherein the bivalent ion is $Mg^{2+}$.

5. The method of claim 1 wherein the blood sample has been frozen before step (a).

6. The method of claim 1, wherein the amplification is performed by polymerase chain reaction (PCR).

7. The method of claim 6 wherein the polymerase used for the enzymatic amplification is selected from the group consisting of *Thermus aquaticus, Thermus thermophilus, Thermococcus litoralis* and *Pyrococcus furiosus*.

8. The method of claim 6 wherein the monovalent and bivalent ion concentrations in the reaction mixture are adjusted with 10X PCR buffer (A).

9. The method of claim 2 wherein the anticoagulant is heparin and the overall monovalent ion concentration in the reaction mixture is adjusted to 10–160 mM.

10. The method of claim 9 wherein the overall monovalent ion concentration in the reaction mixture is adjusted to 10–90 mM.

11. The method of claim 2 wherein the anticoagulant is EDTA and the overall monovalent ion concentration in the reaction mixture is adjusted to 10–135 mM.

12. The method of claim 11 wherein the overall monovalent ion concentration in the reaction mixture is adjusted to 30–80 mM.

13. The method of claim 12 wherein the bivalent ion concentration in the reaction mixture is adjusted to 1.4–5 mM.

14. The method of claim 2 wherein the anticoagulant is citrate and the monovalent ion concentration in the reaction mixture is adjusted to 30–200 mM.

15. The method of claim 14 wherein the monovalent ion concentration in the reaction mixture is adjusted to 60–150 mM.

16. The method of claim 14 wherein said blood sample comprises greater than twenty per cent volume of the reaction mixture and the bivalent ion concentration is adjusted to 3–40 mM.

\* \* \* \* \*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
   ( A ) LENGTH: 26 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

GTGCTGCAGG TGTAAACTTG TACCAG    26

( 2 ) INFORMATION FOR SEQ ID NO:2:

( i ) SEQUENCE CHARACTERISTICS:
   ( A ) LENGTH: 28 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

CACGGATCCG GTAGCAGCGG TAGAGTTG    28

( 2 ) INFORMATION FOR SEQ ID NO:3:

( i ) SEQUENCE CHARACTERISTICS:
   ( A ) LENGTH: 25 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:3:

AGGACCGGGC ATTCTAAGCA GTTTA    25

( 2 ) INFORMATION FOR SEQ ID NO:4:

( i ) SEQUENCE CHARACTERISTICS:
   ( A ) LENGTH: 25 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

CAGTTTCAAC TTGTTTCAGA GGGAA    25

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:5:

CTCTCAATTT TCTAGGGGGA                                                      20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:6:

AGCAGCAGGA TGAAGAGGAA                                                     20

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

TGCTTTGCCC CATGGGACCT CGAG                                                  24

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:8:

GGCGAACACG CTCATCACGG T  21